(12) United States Patent
Gao

(10) Patent No.: US 7,786,457 B2
(45) Date of Patent: Aug. 31, 2010

(54) SYSTEMS AND METHODS OF NON-INVASIVE LEVEL SENSING FOR A SURGICAL CASSETTE

(75) Inventor: Shawn X. Gao, Irvine, CA (US)

(73) Assignee: Alcon, Inc., Hunenberg (CH)

( * ) Notice: Subject to any disclaimer, the term of this patent is extended or adjusted under 35 U.S.C. 154(b) by 189 days.

(21) Appl. No.: 11/477,032

(22) Filed: Jun. 28, 2006

(65) Prior Publication Data
US 2008/0066542 A1   Mar. 20, 2008

(51) Int. Cl.
  G01N 15/06 (2006.01)
  G01N 21/49 (2006.01)
  G01N 21/85 (2006.01)
(52) U.S. Cl. .................. 250/577; 128/867; 606/1; 606/4
(58) Field of Classification Search .......... 250/577; 606/1, 4; 128/897; 347/84–86, 19
  See application file for complete search history.

(56) References Cited

U.S. PATENT DOCUMENTS

| 4,123,227 A | 10/1978 | Heim et al. |
| 4,297,588 A | 10/1981 | Hastbacka |
| 4,395,258 A | 7/1983 | Wang et al. |
| 4,425,794 A | 1/1984 | Duesbury |
| 4,450,722 A | 5/1984 | Keyes, IV et al. |
| 4,493,695 A | 1/1985 | Cook |
| 4,627,833 A | 12/1986 | Cook |
| 4,680,475 A | 7/1987 | Transony et al. |
| 4,703,314 A | 10/1987 | Spani |
| 4,713,051 A | 12/1987 | Steppe et al. |
| 4,758,238 A | 7/1988 | Sundblom et al. |
| 4,773,897 A | 9/1988 | Scheller et al. |
| 4,790,816 A | 12/1988 | Sundblom et al. |
| 4,798,580 A | 1/1989 | DeMeo et al. |
| 4,920,336 A | 4/1990 | Meijer |
| 5,163,900 A | 11/1992 | Wortrich |
| 5,267,956 A | 12/1993 | Beuchat |
| 5,364,342 A | 11/1994 | Beuchat et al. |
| 5,534,708 A | 7/1996 | Ellinger et al. |

(Continued)

FOREIGN PATENT DOCUMENTS

EP   0777111 A1   6/1997

(Continued)

OTHER PUBLICATIONS

Peter Weber: "Optical Sensor Measures Filling Levels in Glass Tubes;" Feinwerktechnik & Messtechnik, 99, No. 1/2 (1991), pp. 31-33 (14 pages).

(Continued)

Primary Examiner—Thanh X Luu
Assistant Examiner—Francis M Legasse, Jr.

(57) ABSTRACT

Embodiments of the present invention provide a system and method for detecting the level of a fluid in a surgical cassette by projecting light from a linear light source into a wall of a cassette. Depending on the amount a light reflected or refracted in the cassette (i.e., due to the cassette material/fluid interface or cassette material/air interface (or other interface)) various portions of a linear sensor array will be more or less illuminated. By examining the illumination of the linear sensor array, the level of fluid in the chamber can be determined.

8 Claims, 10 Drawing Sheets

U.S. PATENT DOCUMENTS

| | | | |
|---|---|---|---|
| 5,747,824 | A | 5/1998 | Jung et al. |
| 5,810,766 | A | 9/1998 | Barnitz et al. |
| 5,880,480 | A | 3/1999 | Ellinger et al. |
| 6,024,428 | A * | 2/2000 | Uchikata ................ 347/7 |
| 6,036,458 | A | 3/2000 | Cole |
| 6,059,544 | A | 5/2000 | Jung |
| 6,206,850 | B1 | 3/2001 | O'Neil |
| 6,267,956 | B1 | 7/2001 | Gomes |
| 6,293,926 | B1 | 9/2001 | Sorenson et al. |
| 6,364,342 | B1 | 4/2002 | Kim |
| 6,561,999 | B1 | 5/2003 | Nazarifar |
| 6,908,451 | B2 | 6/2005 | Brody et al. |
| 6,941,813 | B2 | 9/2005 | Boukhny et al. |
| 7,326,183 | B2 | 2/2008 | Nazarifar et al. |
| 2001/0016711 | A1 | 8/2001 | Sorenson |
| 2001/0035887 | A1 | 11/2001 | Altfather et al. |
| 2003/0202894 | A1 | 10/2003 | Leukanech |
| 2003/0204172 | A1 | 10/2003 | Steppe |
| 2003/0225363 | A1 | 12/2003 | Gordon |
| 2004/0074281 | A1 | 4/2004 | Lobdell et al. |
| 2004/0106915 | A1 | 6/2004 | Thoe |
| 2004/0253129 | A1 | 12/2004 | Sorensen |
| 2005/0065462 | A1 | 3/2005 | Nazarifar |
| 2005/0186098 | A1 | 8/2005 | Davis |
| 2005/0234395 | A1 | 10/2005 | Mackool |
| 2005/0285025 | A1 | 12/2005 | Boukhny et al. |
| 2008/0000485 | A1 | 1/2008 | Williams et al. |
| 2008/0077077 | A1 | 3/2008 | Williams et al. |
| 2008/0103433 | A1 | 5/2008 | Nazarifar et al. |

FOREIGN PATENT DOCUMENTS

| | | |
|---|---|---|
| EP | 0777111 B1 | 9/2003 |
| EP | 1873501 A1 | 1/2008 |
| GB | 1254860 | 11/1971 |
| WO | WO99/20983 | 4/1999 |

OTHER PUBLICATIONS

Excerpts from pp. 3-3, 3-13 & 3-14 of the SeriesTen Thousand® Ocutome® STTOdx™ Cavitron/Kelman® Phaco-Emulsifier® Aspirator Service Manual; Alcon Laboratories, Inc., 1993 (5 pages).

Schematic, PCB, M/A Pneumatic Control; Dwg. No. 940-8040-025; Alcon Surgical, 1990. (1 page).

Schematic, PCB, Photocell, Cassette; Dwg. No. 940-8040-002; CooperVision, 1987. (1 page).

Schematic, PCB, LED, Cassette; Dwg. No. 940-8040-001; CooperVision, 1987. (1 page).

\* cited by examiner

SYSTEMS AND METHODS OF NON-INVASIVE LEVEL SENSING FOR A SURGICAL CASSETTE

TECHNICAL FIELD OF THE INVENTION

The present invention relates to surgical system and methods. More particularly, the present invention relates to a system for sensing the level of fluids in a surgical cassette used in an ophthalmic surgical system.

BACKGROUND OF THE INVENTION

The human eye can suffer a number of maladies causing mild deterioration to complete loss of vision. While contact lenses and eyeglasses can compensate for some ailments, ophthalmic surgery is required for others. Generally, ophthalmic surgery is classified into posterior segment procedures, such as vitreoretinal surgery, and anterior segment procedures, such as cataract surgery. More recently, combined anterior and posterior segment procedures have been developed.

The surgical instrumentation used for ophthalmic surgery can be specialized for anterior segment procedures or posterior segment procedures or support both. In any case, the surgical instrumentation often requires the use of associated consumables such as surgical cassettes, fluid bags, tubing, hand piece tips and other consumables.

A surgical cassette can provide a variety of functions depending on the procedure and surgical instrumentation. For example, surgical cassettes for cataract surgeries (e.g., phacoemulsification procedures) help manage irrigation and aspiration flows into and out of a surgical site. Surgical cassettes can also provide support for fluid bags, a manifold for directing vacuum/pressure to surgical instrumentation, and other functionality.

The fluid levels of the infusion/irrigation chamber and the aspiration chamber of a surgical cassette are measured to determine the amount of remaining fluid for procedure and fluid flow characteristics. Previous chamber fluid level sensing methods require coloring the fluid or using a float to mark the fluid air interface. However, adding color to the fluid is undesirable as it adds additional chemicals to fluids entering the eye. The use of floats is undesirable as floats can stick in a chamber and are sensitive to the orientation of the chamber. Therefore, a need exists for a method and system of non-invasive continuous level sensing that can reduce or eliminate the problems associated with prior art level sensing systems and methods.

SUMMARY OF THE INVENTION

Embodiments of the system and method for continuous non-invasive level sensing of this invention meet these need and others. Embodiments of the present invention provide an apparatus and method for sensing the level of fluid in a surgical chamber. One embodiment of the present invention includes a surgical system comprising a surgical cassette at least partially formed of a cassette material defining a chamber and comprising a first wall and a second wall and a surgical console comprising a cassette receiver to receive the surgical cassette. The surgical console can further include a plurality of vertically arranged light sources to project light into the first wall of the surgical cassette, wherein each of the plurality of light sources is positioned to project a corresponding light ray along a corresponding transmission path that has an angle of incidence with a chamber surface so that at least a majority of the corresponding light ray is reflected if a cassette material/first fluid (e.g. AIR) interface intersects the corresponding transmission path and a majority of the corresponding light ray is not reflected if a cassette material/second fluid (e.g. BSS) interface intersects the corresponding transmission path. Additionally, the surgical console can include a sensor array having a plurality of vertically arranged portions to receive light through the second wall of the surgical cassette and generate an output that indicates an illumination amount of each of the vertically arranged portions.

Another embodiment of the present invention includes a system having a linear light array and a linear sensor array. The linear light array can comprise a first light source to project a first beam of light into a first cassette wall along a first transmission path, wherein the first transmission path has an angle of incidence with a chamber surface so that at least a majority of the first light beam is refracted if a cassette material/first fluid interface intersects the first transmission path; and a second light arranged along a vertical axis with respect to the first light source to project a second beam of light into the first cassette wall along a second transmission path, wherein the second transmission path has an angle of incidence with the chamber surface so that at least a majority, if not all, of the second light beam is reflected if the cassette material/second fluid interface intersects the second transmission path. The linear sensor array can comprise a first portion positioned to receive the first beam of light and a second portion positioned to receive the second beam of light and produce an output signal to indicate whether each of the first and second portions are illuminated.

Yet another embodiment of the present invention includes a method of determining the level of fluid in a surgical cassette comprising emitting a plurality of light beams into a wall of a surgical cassette along parallel vertically spaced transmission paths, detecting the amount of illumination of various vertically arranged portions of a linear sensor array positioned to receive the plurality of light beams, and determining the level of fluid based on the illumination of the various vertically arranged portions of the linear sensor array.

Yet another embodiment of the present invention comprises a system having a surgical cassette at least partially formed of a cassette material defining a chamber and comprising a first wall and a second wall. The system can further include a surgical console that comprises a cassette receiver to receive the surgical cassette, a light source and a sensor. The light source can project a light ray along a transmission path into the first wall of the surgical cassette. The light source is positioned so that at least a majority of the light ray is reflected if a cassette material/first fluid interface intersects the transmission path and a majority of the light ray is not reflected if a cassette material/second fluid interface intersects the transmission path.

The sensor is positioned to receive light through the second wall of the surgical cassette and generate an output that indicates the illumination of the sensor.

Another embodiment of the present invention includes a method of determining the presence of fluid in a surgical cassette that comprises the steps of emitting a light beam into a wall of a surgical cassette at angle incidence to cause a majority of the light beam to reflect at a cassette material/first fluid interface and a majority of the light beam to not reflect at a cassette material/second fluid interface and using an output of a sensor to determine a presence or absence of a liquid at a particular level in a cassette chamber. Depending on the configuration of the cassette, the light may reflect, for example, at a cassette material/liquid interface but not at a cassette material/air interface.

Embodiments of the present invention provide an advantage because the light source and linear sensor array do not directly contact surgical fluid. Moreover, no floating device inside the chamber or coloration of the fluid is required.

Embodiments of the present invention provide another advantage by providing for high resolution continuous level sensing.

Embodiments of the present invention provide another advantage by providing high sensitivity flow rate determinations.

Embodiments of the present invention provide another advantage by determining level based on the transition between pixels of a sensor array defined in an "ON" state and those defined in an "OFF" state. Such embodiments are not sensitive to the sensitivity of the linear sensor array.

BRIEF DESCRIPTION OF THE FIGURES

A more complete understanding of the present invention and the advantages thereof may be acquired by referring to the following description, taken in conjunction with the accompanying drawings in which like reference numbers indicate like features and wherein.

DETAILED DESCRIPTION

Preferred embodiments of the invention are illustrated in the figures, like numerals being used to refer to like and corresponding parts of the various drawings.

Embodiments of the present invention provide a system and method for detecting the level of a fluid in a surgical cassette by projecting light from a linear light source into a wall of a cassette. Depending on the amount a light reflected or refracted in the cassette (e.g., due to the cassette material/liquid interface or cassette material/air interface), various portions of a linear sensor array will be more or less illuminated. By examining the illumination of the linear sensor array, the level of fluid in the chamber can be determined.

Figure 1:
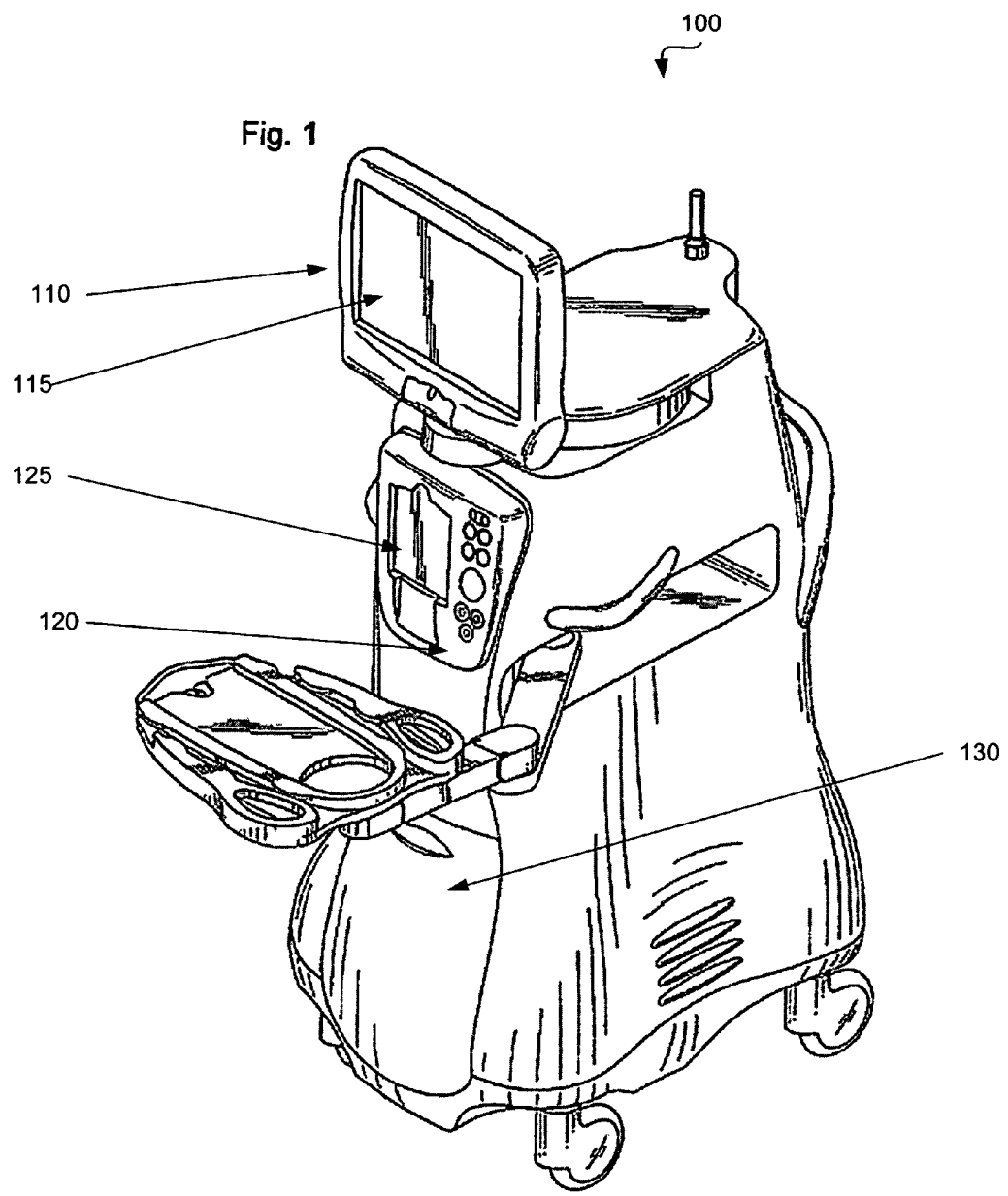
FIG. 1 is a diagrammatic representation of one embodiment of a surgical console.

FIG. 1 is a diagrammatic representation of one embodiment of an ophthalmic surgical console 100. Surgical console 100 can include a swivel monitor 110 that has touch screen 115. Swivel monitor 110 can be positioned in a variety of orientations for whomever needs to see touch screen 115. Swivel monitor 110 can swing from side to side, as well as rotate and tilt. Touch screen 115 provides a graphical user interface ("GUI") that allows a user to interact with console 100.

Surgical console 100 also includes a connection panel 120 used to connect various tools and consumables to surgical console 100. Connection panel 120 can include, for example, a coagulation connector, connectors for various hand pieces, and a cassette receiver 125. Surgical console 100 can also include a variety of user friendly features, such as a foot pedal control (e.g., stored behind panel 130) and other features.

In operation, a cassette (not shown) can be placed in cassette receiver 125. A clamp in surgical console 100 clamps the cassette in place to minimize movement of the cassette during use. The clamp can clamp the top and bottom of the cassette, the sides of the cassette or otherwise clamp the cassette.

Figure 2:
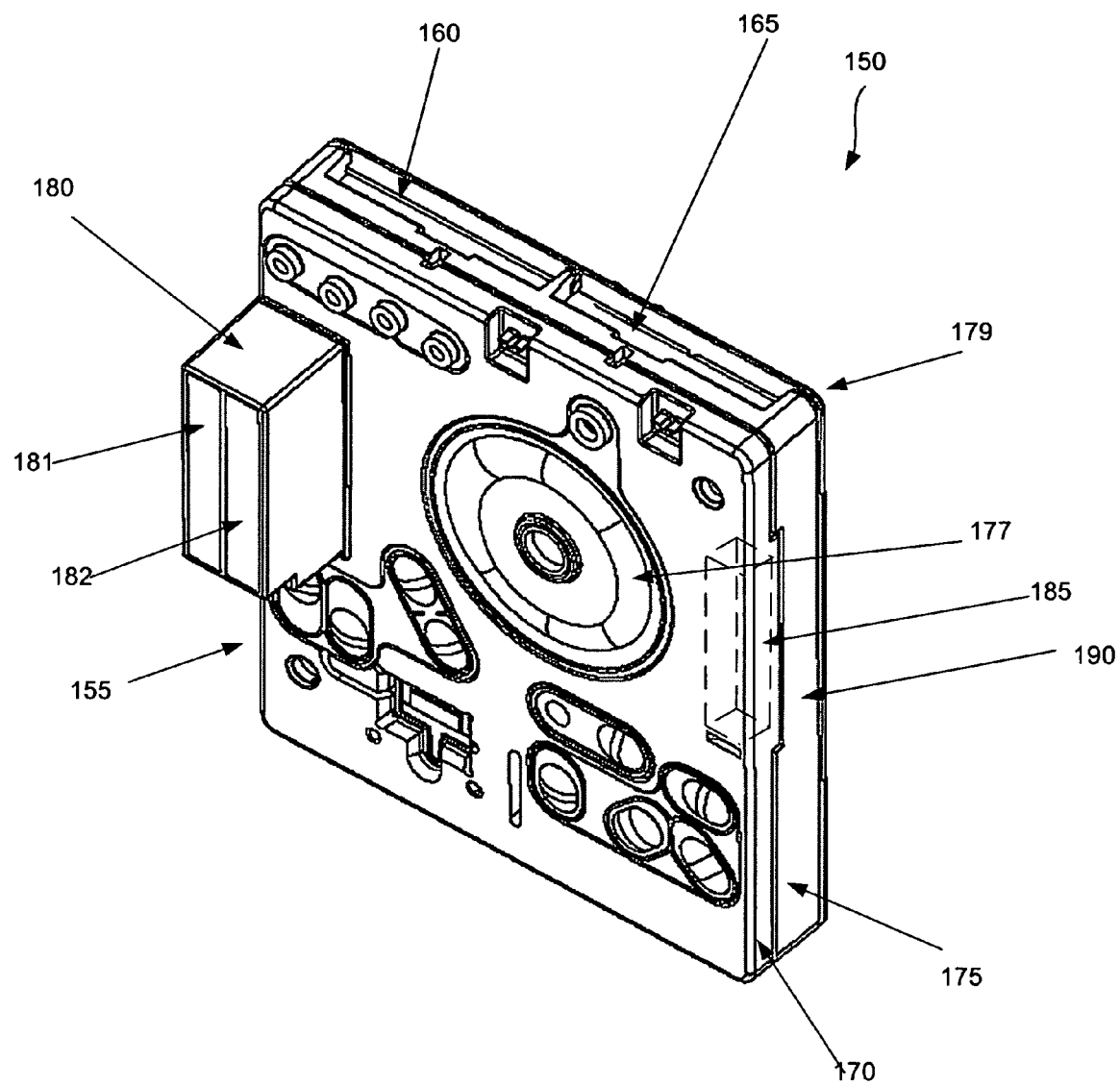
FIG. 2 is a diagrammatic representation of one embodiment of a surgical cassette.

FIG. 2 is a diagrammatic representation of one embodiment of a surgical cassette 150. Cassette 150 can provide a closed system fluidic device that can be discarded following a surgical procedure. Cassette 150 can include a cassette body 155 and portions that interface with the clamp (e.g., indicated generally at clamping zones 160 and 165) projecting from the cassette body 155. Cassette 150 can be formed of ABS plastic or other suitable material. In the embodiment shown, cassette 150 is formed from three primary sections: an inner or surgical console interface section 170 that faces the surgical console when cassette 150 is inserted into surgical console 100, a middle section 175 and a cover plate 179. The various sections of cassette 150 can be coupled together via a press fit, interlocking tabs, chemical bonding, thermal bonding, mechanical fasteners or other attachment mechanism known in the art. In other embodiments, cassette 150 can be formed of a single piece or multiple pieces.

Surgical console interface section 170 can face the console during use and provide an interface for fluid flow channels (e.g., flow channel 177 for the peristaltic pump provided by an elastomeric pump membrane), valves (e.g., infusion/aspiration valves), and other features to manage fluid flow. Cassette 150 can also attach to a fluid bag (not shown) to collect fluids during a procedure.

Surgical cassette 150, according to various embodiments of the present invention, includes chambers to hold fluids for aspiration and infusion. For example, chamber cartridge 180 can include two infusion chambers 181/182. A third chamber 185 can be internal to cassette 150 on the opposite side of cassette 150 from chamber cartridge 180 (e.g., at the side of cassette 150 indicated by 190). According to one embodiment, the level of fluid in the chambers can be determined in a noninvasive manner. As described below, light can be projected into the chamber walls using a vertical light source. Depending on the reflection or refraction of light at the chamber, a vertical sensor array will detect or not detect light at various points along the array's vertical axis. Based on the transition between illuminated and nonilluminated portions of the sensor array, the level of the fluid in the chamber can be detected.

Figure 3:
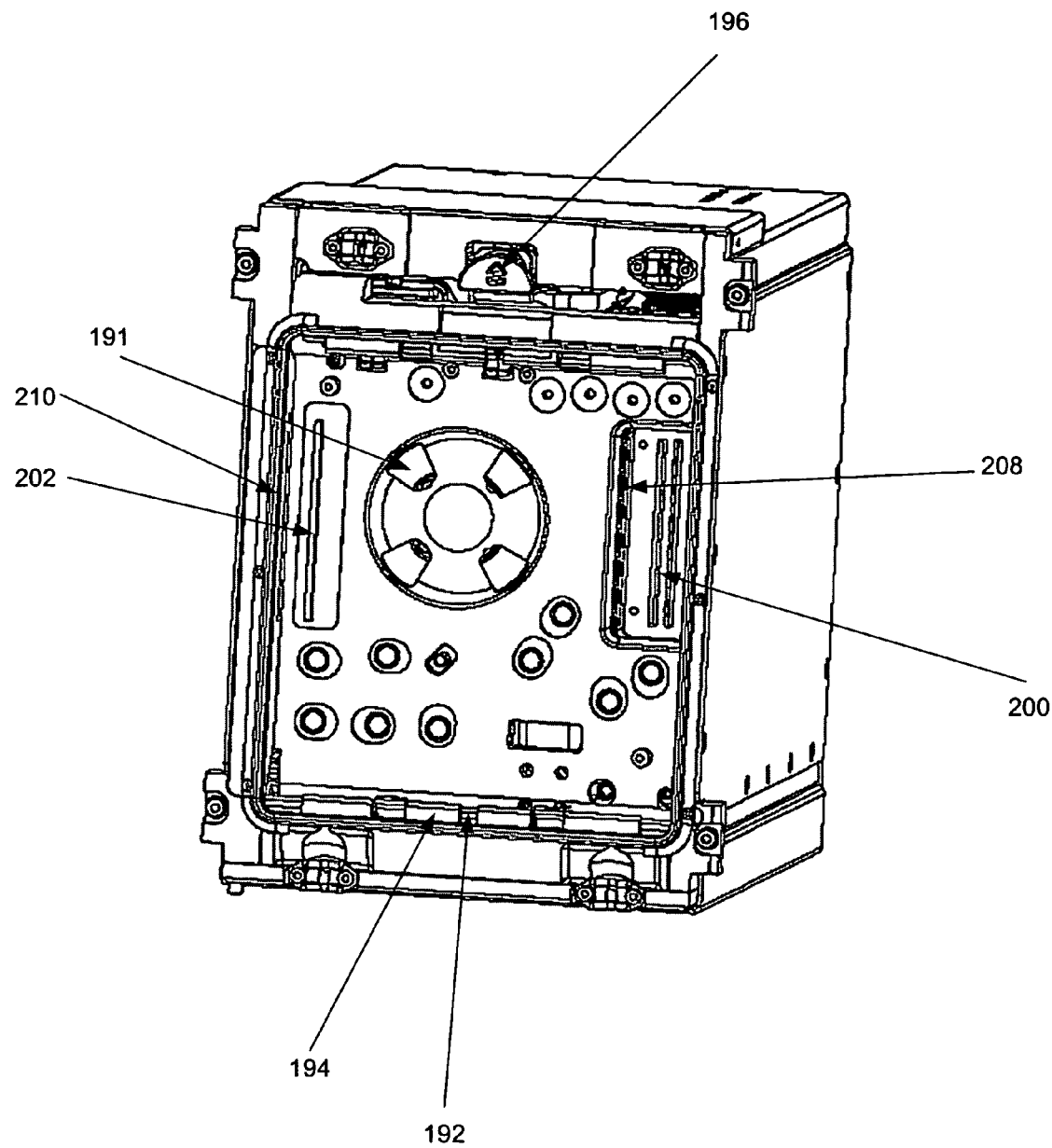
FIG. 3 is a diagrammatic representation of one embodiment of a cassette receiver.

FIG. 3 is a diagrammatic representation of one embodiment of cassette receiver 125 without a cassette. Cassette receiver 125 can have various pneumatic input and output ports to interface with the surgical cassette. Cassette receiver 125 can further include an opening to allow peristaltic pump rollers 191 to contact the surgical cassette during operation. One embodiment of a peristaltic pump and complimentary cassette is described in U.S. Pat. No. 6,293,926 to Sorensen, which is hereby fully incorporated by reference herein.

Figure 9A:
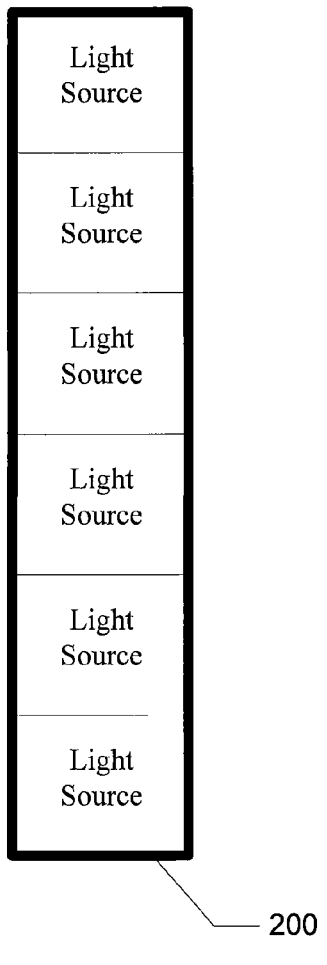
FIG. 9a is a representation of an embodiment of a linear light source.
Figure 9B:
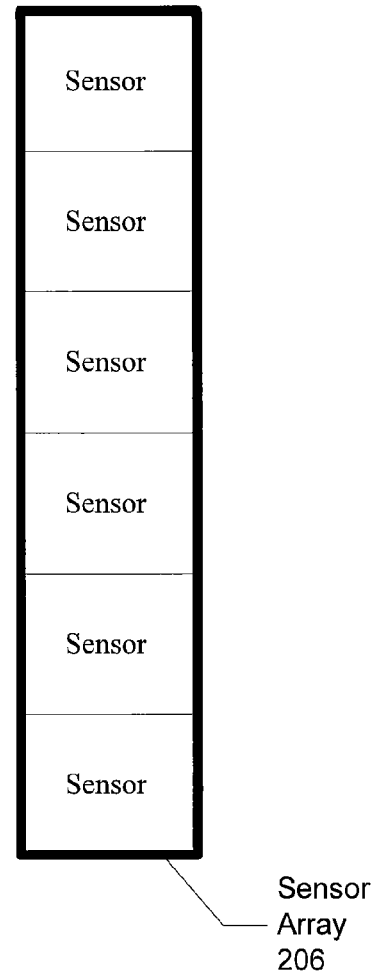
FIG. 9b is a representation of an embodiment of a linear sensor array.
Figure 9C:
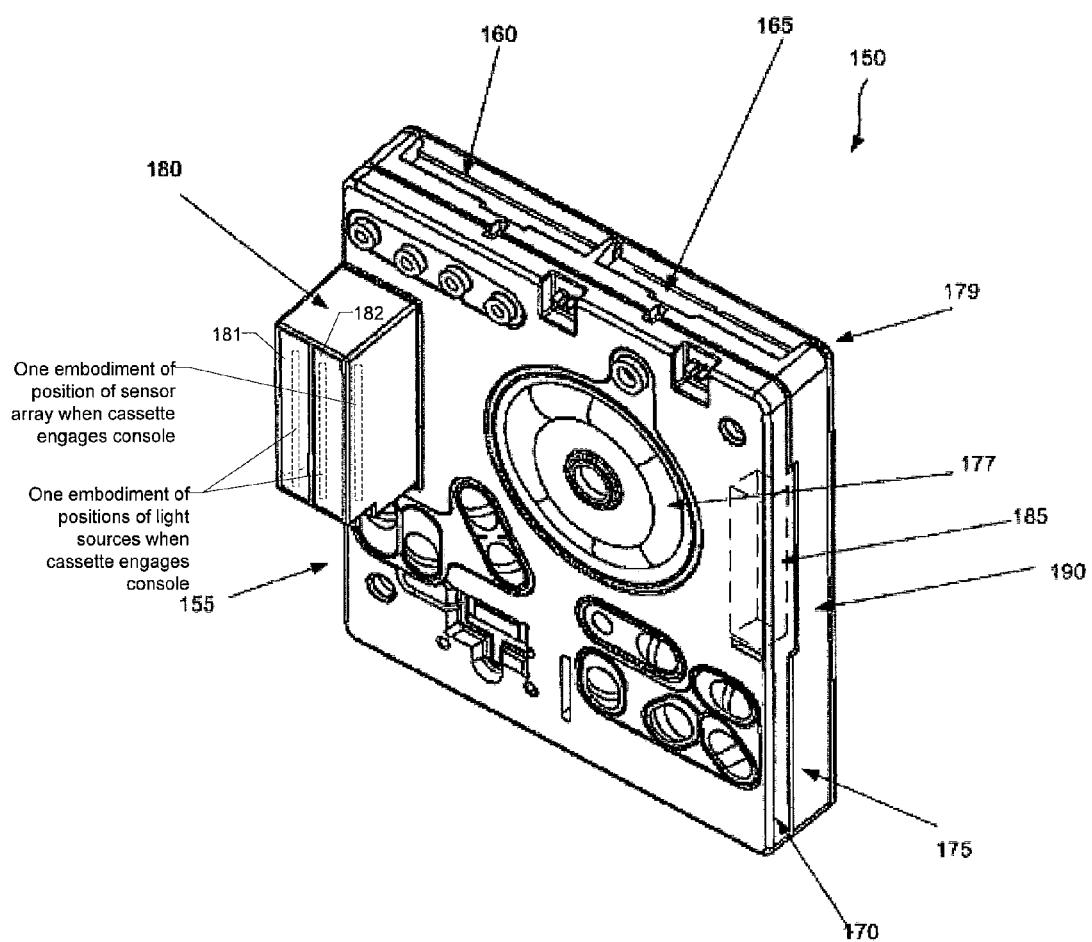
FIG. 9c is a representation of an embodiment of a surgical cassette with dashed lines for the light source and sensor array position when the cassette is received into the console.

The surgical cassette, in the embodiment of FIG. 3, is held in place by a clamp having a bottom rail 192 and a top rail (not shown). Each rail can have outer clamping fingers (e.g., clamp finger 194) that contact the cassette in corresponding clamping zones and inner clamping fingers to locate the cassette during insertion and push the cassette out of cassette receiver during release. A release button 196 is pressed to initiate release of the cassette from the clamp. Cassette receiver 125 can include linear light sources to project light into the walls of the cassette chambers and sensor arrays to detect the light refracted through the chamber (or reflected from the chamber wall). Each linear light source can include a plurality of light sources vertically arranged (i.e., to project light along vertically spaced transmission paths) and positioned to project light into a wall of the cassette. For example, linear light source 200 can project light into chambers 181/182. Linear light source 200 can contain a first set of light sources (for example, see FIG. 9a) aligned to project light into chamber 181 and a second set of light sources arranged at a 90 degree angle (or other angle) from the first set of light sources to project light into chamber 182. Similarly, linear light source 202 can project light into the walls of chamber 185. Respective linear sensor arrays can receive light refracted through the chamber or reflected at the chamber surface. In this example, sensor array 206 (shown, for example, in FIG. 4 and FIGS. 9b-9c) can receive light from light source 200 projected at chamber 181, a sensor array located in wall 208 can receive light from light source 200 projected at chamber 182 and a sensor array in wall 210 can receive light from light source 202. Each sensor array can include vertically arranged portions to receive light through the wall of the cassette chamber. The vertically arranged portions can be, for example, pixels, separate sensors or other mechanisms for sensing illumination.

The configuration of FIG. 3 is provided by way of example. The form factor of cassette receiver 125, placement and number of input/output ports and other features of cassette receiver 125 can depend on the surgical console 100, surgical procedure being performed or other factors.

Figure 4:
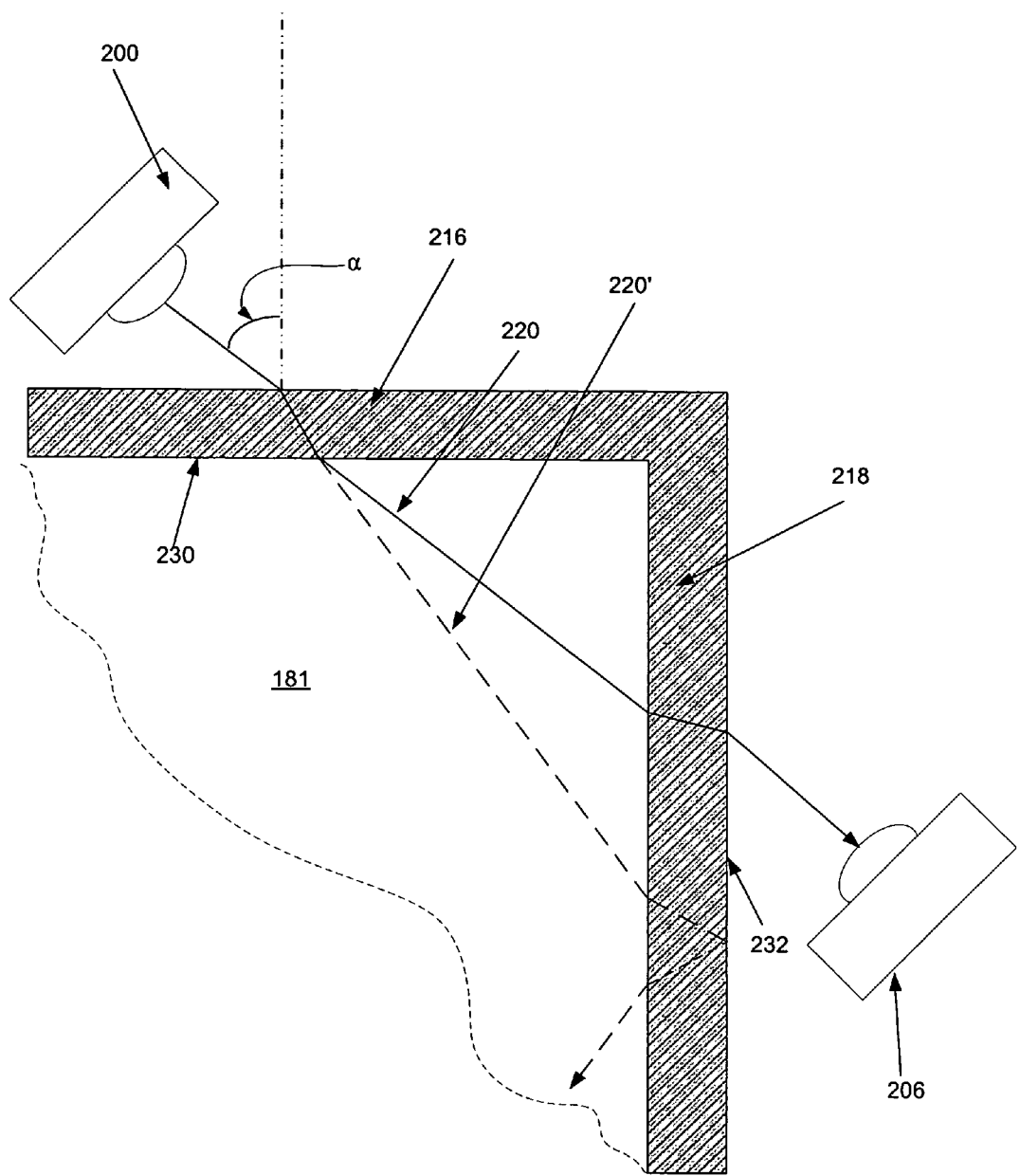
FIG. 4 is a diagrammatic representation of one embodiment of a top-view of a chamber with a linear light source and sensor array.

FIG. 4 is a diagrammatic representation of a top view of one embodiment of a chamber 181 with light source 200 and sensor 206. Walls 216/218 of chamber 181 that face light source 200 and sensor 206, according to one embodiment, are transparent or opaque. According to one embodiment of the present invention, light source 200 can be a linear light source (i.e., a continuous light source), such as a linear LED light source, that produces light at various vertical points and sensor 206 can be a linear sensor array (i.e., a continuous sensor array), such as a linear photodiode, that detects light emitted by light source 200 at various vertical locations. One example of a linear sensor array 206 is the TAOS TSL208R linear sensor array by Texas Advanced Optoelectronic Systems of Plano, Tex., which has a resolution of 200 dots per inch (DPI). Linear light source 200 and linear sensor array 206 are connected to a circuit (not shown). According to one embodiment, linear light source can also include lights to project light into another chamber (e.g., chamber 182 of FIG. 2). Preferably, the light produced by light source 200 provides uniform parallel light beams that have a primarily horizontal transmission path.

In operation, linear light source 200 acts an emitter to emit light while linear sensor 206 acts as receiver. The angle of incidence α of light to chamber wall 216 can be selected so that light rays illuminate sensor 206 when passing through air in the chamber, but provide less than a threshold amount of light when passing through BSS fluid in the chamber. As an example, FIG. 4 illustrates the behavior of a light ray 220 passing through air in chamber 181 and 220' passing through BSS fluid in chamber 181. In the first case, light-beam 220 penetrates wall 216, passes through the air in the top of chamber 181, through chamber wall 218 and illuminates portions of linear sensor array 206. On the other hand, light-beam 220' is refracted at surface 230 when it enters the BSS fluid (e.g., at the ABS/BSS interface). The refracted light beam 220' is further reflected at surface 232 when it reaches adjacent wall 218 to miss the pixels of sensor array 206. With an appropriate α, the reflection at surface 232 can become total reflection because the refraction index of the cassette material (e.g. ABS plastic, acrylic or other plastic) is larger than that of air. In this case, the light is completely reflected, preventing the light beam from reaching the portions of linear sensor array 206 aligned with the BSS fluid in the chamber. Therefore, the pixels aligned with the BSS fluid will be dark. Thus, most of the light is not reflected when the transmission path of the light is intersected by the ABS/air interface but a majority of the beam (if not all) is reflected when the transmission path is intersected by the ABS/BSS interface.

The electronic circuit can compare the output of different portions of linear sensor array 206 (e.g., pixels or other sensor elements) with a threshold to determine if that portion of linear sensor array 206 is "ON" (associated with air) or "OFF" (associated with the liquid). The transition between the "ON" portion and the "OFF" portions of linear sensor array 206 marks the fluid level. It should be noted however, other edge detection mechanisms can be employed, such as linear interpolation.

The appropriate incident angle α of the light is determined by the refraction index of the first fluid (e.g., air or other fluid) and the second fluid (e.g., BSS fluid or other fluid) and the cassette material (e.g., ABS plastic or other material). Preferably, α is chosen so that the light beam can pass through the first fluid to reach sensor array 206 but is completely reflected when it travels through the second fluid. In other embodiments in which the light beam is not totally reflected, the predetermined threshold can be set to compensate for the amount of light that does reach sensor array 206 through the second fluid. The predetermined threshold can also be adjusted to compensate for ambient light sources, light bleed from other sources and other factors that may cause a portion of sensor array 206 to output a signal in the "OFF" state.

Figure 5:
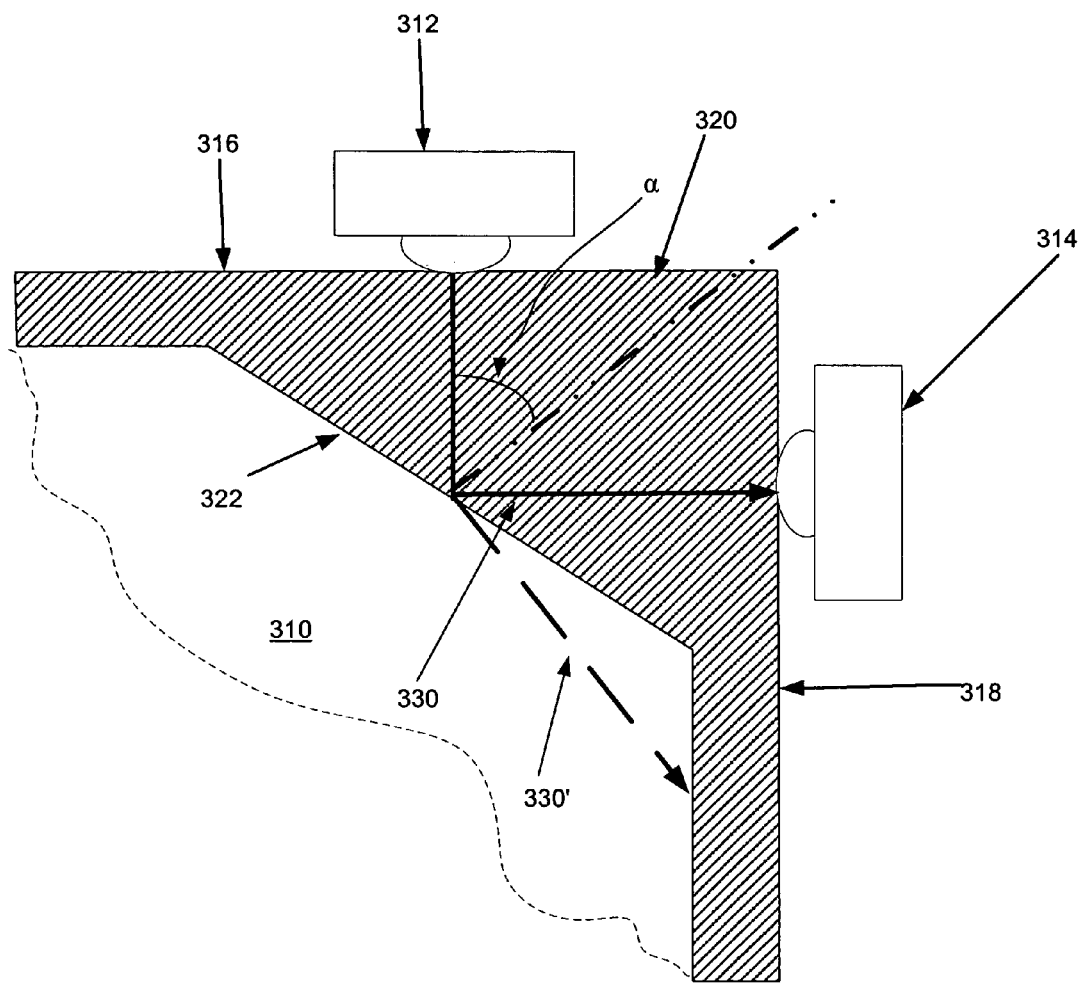
FIG. 5 is a diagrammatic representation of another embodiment of a top-view of a chamber with a linear light source and sensor array.

FIG. 5 is a diagrammatic representation of another embodiment of a chamber 310 with light source 312 and sensor 314. Walls 316/318 of chamber 310 that face light source 312 and sensor 314, according to one embodiment, are transparent or opaque. According to one embodiment of the present invention, light source 312 can be a linear light source (i.e., a continuous light source), such as a linear LED light source, that produces light along a vertical axis and sensor 314 can be a linear sensor array (i.e., a continuous sensor array), such as a linear photodiode, that detects light emitted by light source 312 along a vertical axis. Linear light source 312 and linear sensor array 314 are connected to a circuit (not shown).

Linear light source 312 is mounted to one side of the chamber illuminating chamber 310 perpendicular to wall 316. Linear sensor array 314 is mounted vertically on the adjacent side wall 318 of the chamber. Chamber 310 has a prism shaped corner 320 at the intersection of wall 316 and 318. Incident angle α can be selected so that light beams from light source 312 totally reflect from surface 322 to hit linear sensor array 314 when the light beam hits surface 322 at a point that has a first fluid on the other side (Refraction index of ABS is about 1.5, Refraction index of AIR is about 1.0).

But the majority of the light beams refract at surface 322 to miss linear sensor array 314 when the light beam hits surface 322 at a point that has a second fluid on the other side (Refraction index of ABS is about 1.5, Refraction index of BSS is about 1.3). Put another way, a large portion or all the light reflects at surface 322 when the transmission path of the light is intersected by the cassette material/first fluid interface but a small portion of light beams is reflected if the transmission path is intersected by the cassette material/second fluid interface.

As an example, FIG. 5 illustrates the behavior of a light ray 330 primarily reflecting at the air/plastic interface at surface 322 of chamber 310 and light ray 330' primarily refracting into chamber 310 at surface 322. In the first case, light-beam 330 penetrates wall 316, passes through the plastic in corner 320, and reflects at the plastic/air interface of surface 322. On the other hand, a majority of light-beam 330' is refracted at surface 322 at the cassette material/BSS fluid interface, though some of light-beam 330' may also be reflected. In this example, the strongly reflected light (e.g., beam 330) illuminates linear sensor array 314 indicating the presence of air at that level.

Figure 6:
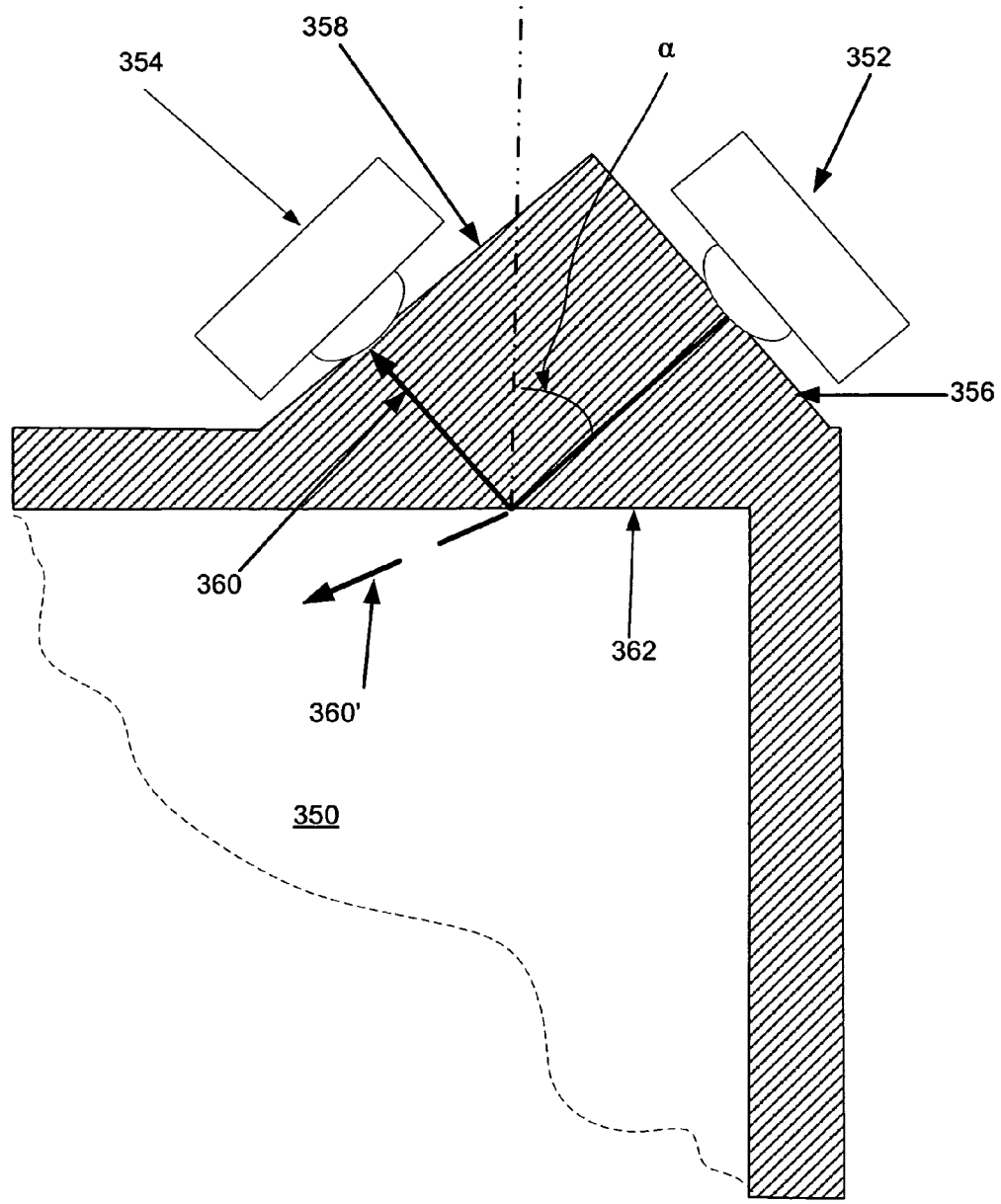
FIG. 6 is a diagrammatic representation of yet another embodiment of a top-view of a chamber with a linear light source and sensor array.

FIG. 6 illustrates another embodiment of reflective-beam level sensing. FIG. 6 is a diagrammatic representation of another embodiment of a chamber 350 with light source 352 and sensor 354. Walls 356/358 of the cassette that face light source 352 and sensor 354, according to one embodiment, are transparent or opaque. According to one embodiment of the present invention, light source 352 can be a linear light source (i.e., a continuous light source), such as a linear LED light source, that produces light along a vertical axis and sensor 354 can be a linear sensor array (i.e., a continuous sensor array), such as a linear photodiode, that detects light emitted by light source 352 along a vertical axis. Linear light source 352 and linear sensor array 354 are connected to a circuit (not shown).

Linear light source 352 is mounted to wall 356. Linear sensor array 354 is mounted vertically to the wall 358. The incident angle α can be selected so that light beams from light source 352 totally reflect from surface 362 to hit linear sensor array 354 when the light beam hits surface 362 at a point that has a first fluid on the other side, but refracts at surface 362 to miss linear sensor array 354 when the light beam hits surface 362 at a point that has a second fluid on the other side due to the fact that ABS has a refraction index of about 1.5, BSS has a refraction index of about 1.3 and air has a refraction index of about 1.0.

Returning example of an ABS cassette having chamber 350 containing air and BSS fluid, since the top of the chamber will contain the air, the upper portion of surface 362 will be an ABS/AIR interface, while the bottom portion of surface 362 will be an ABS/BSS interface. Thus, at surface 362, there are two different optical interfaces. The light beams from linear light source 352 arrive at surface 362 at an incident angle α. Part of the beam can be reflected at surface 362 and received by linear sensor array 354 while part can be refracted into chamber 350.

As an example, FIG. 6 illustrates the behavior of a light ray 360 primarily reflecting at the air/plastic interface at surface 362 of chamber 340 and light ray 360' primarily refracting into chamber 350 at surface 362. In the first case, light-beam 360 penetrates wall 356, passes through the plastic, and reflects at the plastic/air interface of surface 362. On the other hand, light-beam 360' is refracted at surface 362.

Figure 7:
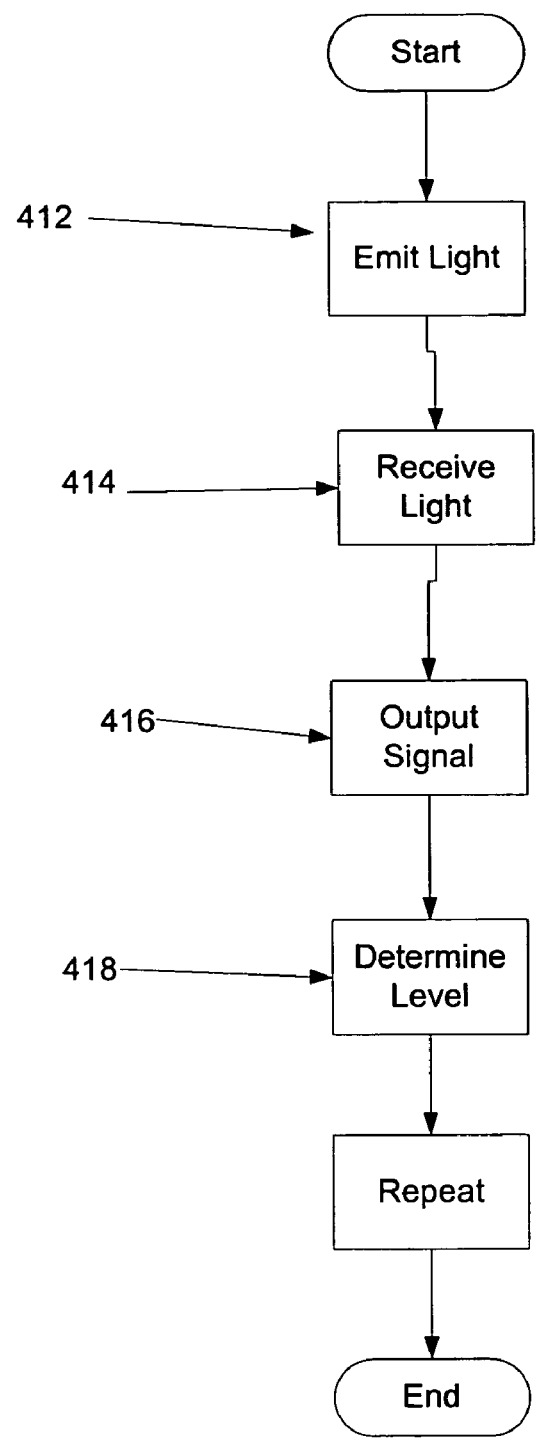
FIG. 7 is a flow chart illustrating one embodiment of a method for level sensing.

FIG. 7 is a flow chart illustrating one embodiment of a method for determining the level of fluid in a chamber. A plurality of light sources (e.g., LEDs or other light sources) project light into the wall of a chamber (step 412) along transmission paths. If the transmission path of a light ray is intersected by a cassette material/first fluid interface, a majority, if not all, of the light ray can be reflected, whereas if the transmission path is intersected by the cassette material/second fluid interface, a majority of the light ray is not reflected. Using the example of FIG. 4, if a light ray is intersected by the ABS/BSS interface (e.g., at surface 230), a majority, if not all, of the light ray is reflected at surface 232. Using the example of FIGS. 5 and 6, on the other hand, if a light ray is intersected by the ABS/Air interface, a majority, if not all, of the light ray is reflected.

A linear sensor array receives some portion of the light projected by the light sources (step 414) and outputs a signal indicating the amount of light received at various portions of the sensor array (e.g., at various pixels of the array) (step 416). At step 418, an edge detection scheme is applied to the output of the linear sensor array to determine which portions of the linear sensor array are sufficiently illuminated to indicate the presence/absence of fluid at the corresponding level in the chamber. According to one embodiment, the output of different portions of the linear sensor are compared with a threshold to determine if that portion of linear sensor is in a first state (e.g., associated with air) or in a second state (e.g., associated with the fluid). The transition between the first state and second state portions of the linear sensor array marks the fluid level. It should be noted however, other edge detection mechanisms can be employed, such as linear interpolation.

The steps of FIG. 7 can be repeated as needed or desired and the level information updated continuously (e.g., at each processor cycle, instructions loop cycle or other period of time). Changes in level information can indicate flow of fluid from the chamber. More specifically, flow rate is proportional to A*dL/dt, where A is the cross-sectional area of the chamber and dL/dt is the change in level over time. Because only one corner of a chamber need be used, the cross-sectional area of the chamber A of the chamber can be minimized. Thus, the sensitivity of the flow rate determination is improved. A reduced cross-section can also reduce the sloshing effects of the fluid in the chamber due to bumping the cassette.

Figure 8:
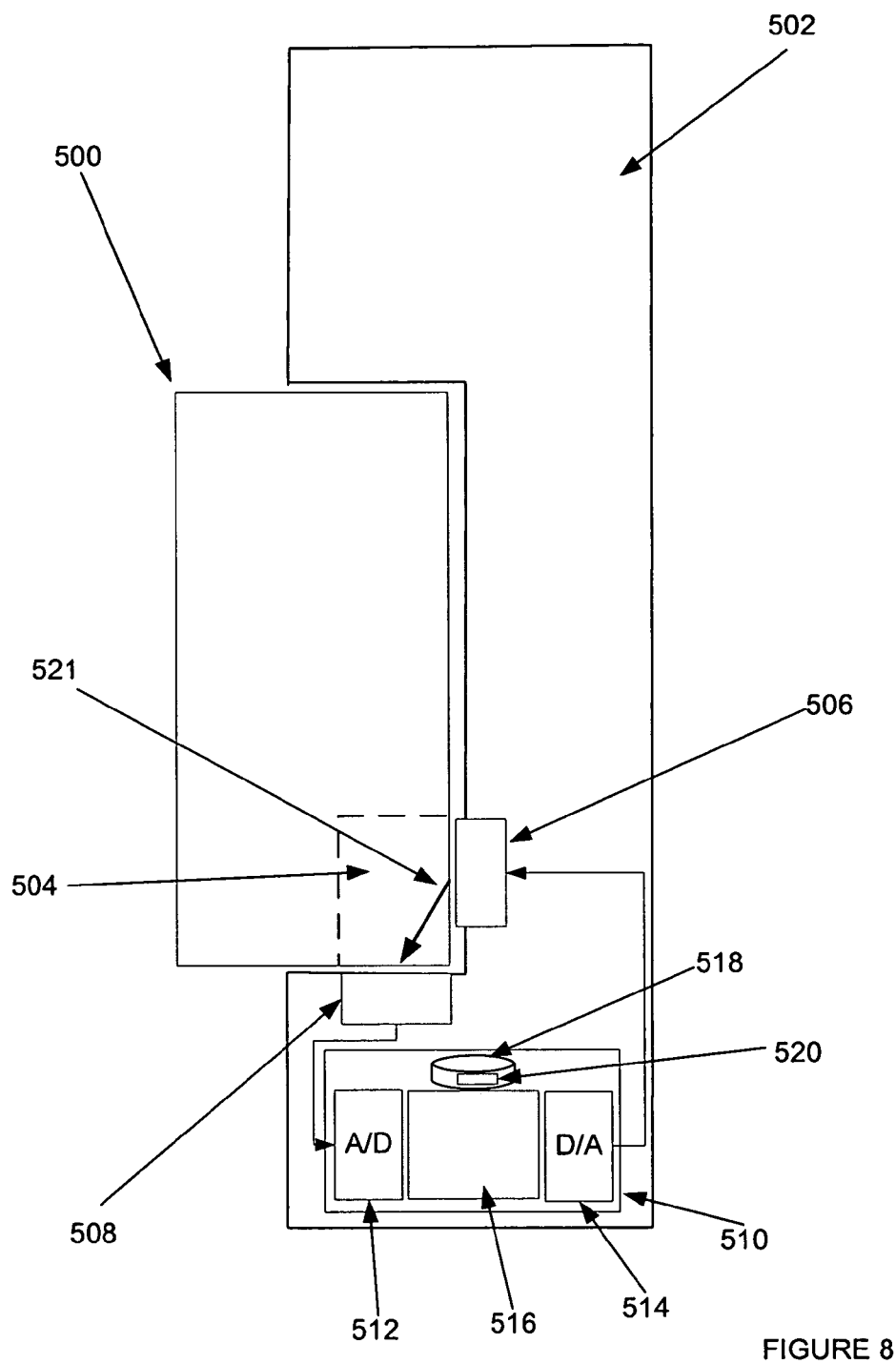
FIG. 8 is a diagrammatic representation of a surgical cassette and console employing the fluid level sensor of the present invention.

FIG. 8 is a schematic representation of a top view of a surgical cassette and console employing the fluid level sensor according to one embodiment of the present invention. Cassette 500 is installed in console 502. Chamber 504 is part of the cassette 500. Linear light source 506 and linear sensor array 508 are part of the console. The light source 506 projects light beam 521 into the wall of cassette 500 with an appropriate incident angle. The linear sensor array 508 is positioned to receive the light beam from the light source. Both the light source and linear sensor array are attached to a controller 510.

Controller 510 can be any suitable controller known in the art including DSP, ASIC, RISK or CPU based controllers. Controller 510 can include an analog to digital (A/D) converter 512 to convert analog signals from linear sensor array 508 to digital signals. Additionally, controller 510 can include a digital to analog (D/A) converter 614 to convert digital control signals to analog signals to control the intensity of lights in light source 506. A processor 516, such as a DSP, ASIC, RISK, microcontroller or CPU or other suitable processor can access a set of instructions 520 and computer readable memory 518. The computer readable memory can be RAM, ROM, magnetic storage, optical storage or other suitable memory and can be onboard or be accessible by processor 516. The processor 516 can execute instructions 520 to process digital inputs to determine the level of fluid in a chamber as discussed above. Controller 510 can optionally communicate with other components of console 502 that provide additional functionality. Other embodiments of the present invention can use any suitable controller for determining the level of fluid in a chamber.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed in the following claims.

The invention claimed is:

1. A system comprising:
a cassette receiver to receive a surgical cassette; wherein the surgical cassette is at least partially formed of a cassette material defining a first chamber comprising a first wall and a second wall and a second chamber, adjacent to the first chamber, comprising a third wall and a fourth wall; and
a first light source to project light along a transmission path into the first wall of the surgical cassette, wherein the light source is positioned so that at least a majority of the light is reflected if a cassette material/first fluid interface intersects the transmission path and a majority of the light is not reflected if a cassette material/second fluid interface intersects the transmission path; and
a first sensor to receive reflected light through the second wall of the surgical cassette and generate an output that indicates illumination of the sensor;
wherein the first light source is mounted in a first wall of the cassette receiver;
wherein the first sensor comprises a plurality of portions mounted in a second wall of the cassette receiver;
a second light source to project light along a transmission path into the third wall of the surgical cassette, wherein the second light source is positioned so that at least a majority of the light is reflected if a cassette material/first fluid interface intersects the transmission path and a majority of the light is not reflected if a cassette material/second fluid interface intersects the transmission path; and
a second sensor to receive reflected light through the fourth wall of the surgical cassette and generate an output that indicates illumination of the sensor;
wherein the second light source is mounted in a third wall of the cassette receiver;
wherein the second sensor comprises a plurality of portions mounted in a fourth wall of the cassette receiver;
wherein the output of the first and second sensors indicate respective illumination amounts of each of the sensor portions in the respective first and second sensors; and
wherein the second wall of the cassette receiver and the first wall of the cassette receiver meet at a corner of the cassette receiver;
wherein the first wall of the first chamber and the second wall of the first chamber meet at a corner of the first chamber;
wherein the third wall of the second chamber and the fourth wall of the second chamber meet at a corner of the second chamber.

2. The surgical system of claim 1, wherein the first sensor is arranged to receive light through the first chamber.

3. The surgical system of claim 1, wherein the first sensor is arranged to receive light reflected from the cassette material/first fluid interface.

4. The surgical system of claim 1, wherein the cassette material/first fluid interface is a cassette material/AIR fluid interface.

5. The surgical system of claim 1, wherein the surgical cassette comprises a prism shaped corner having an inner surface defining a portion of the chamber.

6. The surgical system of claim 1, further comprising a controller operable to determine a presence of fluid at a level in the first and second chambers based on the respective output of the first and second sensors.

7. The surgical console of claim 1, wherein the third wall of the cassette receiver and the first wall of the cassette receiver are integrated in a single wall.

8. The surgical system of claim 4, wherein the cassette material/second fluid interface is a cassette material/Liquid interface.

* * * * *